United States Patent [19]
Yoshioka et al.

[11] Patent Number: 5,271,945
[45] Date of Patent: Dec. 21, 1993

[54] SUSTAINED RELEASE MICROCAPSULE FOR WATER SOLUBLE DRUG

[75] Inventors: Toshio Yoshioka, Hyogo; Hiroaki Okada, Osaka; Yasuaki Ogawa, Kyoto, all of Japan

[73] Assignee: Takeda Chemical Industries, Ltd., Osaka, Japan

[21] Appl. No.: 746,203

[22] Filed: Aug. 15, 1991

Related U.S. Application Data

[63] Continuation of Ser. No. 374,874, Jul. 3, 1989, abandoned.

[30] Foreign Application Priority Data

Jul. 5, 1988 [JP] Japan .................. 63-167490

[51] Int. Cl.⁵ .................. A61K 9/52; A61K 9/66; B01J 13/08; B01J 13/12
[52] U.S. Cl. .................. 424/489; 264/4.1; 264/4.6; 424/452; 424/455; 424/462; 424/499; 424/501; 428/402.21; 428/402.22; 514/800; 514/963
[58] Field of Search .................. 264/4.1; 428/402.21, 428/402.22; 424/452, 455, 462, 489; 514/963

[56] References Cited

U.S. PATENT DOCUMENTS

| | | | |
|---|---|---|---|
| 4,205,060 | 5/1980 | Monsimer et al. | 428/402.22 X |
| 4,479,911 | 10/1984 | Fong | 264/4.6 |
| 4,483,807 | 11/1984 | Asano et al. | 428/177 X |
| 4,671,954 | 6/1987 | Goldberg et al. | 514/963 X |
| 4,728,512 | 3/1988 | Mehta et al. | 424/462 X |
| 4,917,893 | 4/1990 | Okada et al. | 514/963 X |
| 4,954,298 | 9/1990 | Yamamoto et al. | 264/4.6 |

FOREIGN PATENT DOCUMENTS

| | | |
|---|---|---|
| 0052510 | 5/1982 | European Pat. Off. |
| 0145240 | 6/1985 | European Pat. Off. |
| 0190833 | 8/1986 | European Pat. Off. |
| 0256726 | 2/1988 | European Pat. Off. |
| 0263490 | 4/1988 | European Pat. Off. |
| 0302582 | 2/1989 | European Pat. Off. |
| 2128087 | 4/1984 | United Kingdom ......... 424/455 |

OTHER PUBLICATIONS

"Preparation of Microcapsule", Patent Abstracts of Japan, vol. 12, No. 297 Aug. 12, 1988.

*Primary Examiner*—Richard D. Lovering
*Attorney, Agent, or Firm*—Wegner, Cantor, Mueller & Player

[57] ABSTRACT

Sustained release microcapsules including a water soluble drug and an organic basic substance as a drug retaining substance of this invention not only have a high rate of incorporation (trapping rate), but also show little initial release so that they can be administered safely and bring about persistent, stable sustained release.

5 Claims, No Drawings

SUSTAINED RELEASE MICROCAPSULE FOR WATER SOLUBLE DRUG

This application is a continuation of U.S. application Ser. No. 07/374,874, filed Jul. 3, 1989, now abandoned.

This invention relates to sustained release microcapsules containing water soluble drugs.

Various drug forms have been proposed for such drugs that are required to be given over a long period. Microcapsulation disclosed in the EP-A-0052510 is based on phase separation using coacervating agents such as mineral oil and vegetable oil. However, microcapsules prepared by this method are apt to cause coalescence due to cohesion among particles or to form cracks during the course of preparation, which leads to decreased redistribution and increased initial burst. Particularly when the drugs to be included are water soluble, initial burst is hardly avoidable.

The EP-A-0145240 discloses a method for preparation of microcapsules based on drying in water; according to this method, drugs can be included efficiently in microcapsules by increasing the viscosity in the internal water phase, or by increasing the viscosity of the W/O emulsion by addition of a carrier, or as a result of interaction with a drug added.

Requirements for microcapsules prepared for administration of a drug to organisms are diversified as the effect of microcapsules is greatly dependent on the interaction with the innate functions of organisms. For use in medicines, microcapsules which can satisfy the diversified requirements as far as possible have been wished for.

Under these circumstances it cannot be said that a satisfactory effect is always attained with the known microcapsules.

For example, most of the water soluble lower molecular weight drugs and some of the water soluble polymer drugs which have been included in microcapsules are occasionally released in excess over the necessary amount shortly after administration so that the release deviates greatly from the sustained release at a constant rate, which may cause troubles in practical application of a medicine.

Under these circumstances the inventors found that microcapsules with excellent properties with little initial burst can be obtained efficiently by addition of basic drug retaining substance as the result of their researches for development of sustained release preparations of various water soluble drugs, and have completed this invention after further researches.

Namely, this invention provides sustained release microcapsules of a water soluble drug, which contains a water soluble drug and an organic basic substance as a drug retaining substance and wherein the wall is made of a polymer.

The water soluble drugs used in this invention are those with high hydrophilicity and low oil-water partition coefficient. Those with low oil-water partition coefficient mean those for which the coefficient of, for example, octanol/water partition is 0.1 or less.

The said water soluble drug includes, for instance, physiologically active polypeptides, other antibiotics, antitumor agents, antipyretics, analgesics, antiphlogistics, antitussive and expectorant agents, sedatives, muscle relaxants, antiepileptics, antiulcer agents, antidepressants, antiallergic agents, cardiotonics, antiarrhythmic agents, vasodilators, hypotensive diuretics, antidiabetic drugs, anticoagulants, hemostatics, antitubercular agents, hormone preparations, and narcotic antagonists.

The physiologically active polypeptides are desirably those composed of two or more amino acids with a molecular weight of about 200 to 100,000.

The said peptides are exemplified by luteinizing hormone-releasing hormone (LH-RH) and the derivatives thereof [U.S. Pat. No. 3,853,837, ibid. U.S. Pat. No. 4,008,209, ibid. U.S. Pat. No. 3,972,859, ibid. U.S. Pat. No. 4,234,571, British Patent No. 1,423,083, Proc. Natl. Acad. Sci. U.S.A. Vol. 78, p.6509–6512 (1981)], LH-RH antagonists (U.S. Pat. No. 4,086,219, ibid. U.S. Pat. No. 4,124,577, ibid. U.S. Pat. No. 4,253,997, ibid. U.S. Pat. No. 4,317,815), insulin, somatostatin, somatostatin derivatives (U.S. Pat. No. 4,087,390, ibid. U.S. Pat. No. 4,093,574, ibid: U.S. Pat. No. 4,100,117, ibid. U.S. Pat. No. 4,253,998), growth hormone, somatomedin, prolactin, adrenocorticotrophic hormone (ACTH), melanocyte-stimulating hormone (MSH), thyrotropin releasing hormone (TRH) and the salts and derivatives thereof (Japanese Patent Application Laid-Open No. 121273/1975, ibid. No. 116465/1977), thyroid stimulating hormone (TSH), luteinizing hormone (LH), follicle stimulating hormone (FSH), vasopressin, vasopressin derivatives (desmopressin [Acta. Med. Scand., Vol. 192, 21–27 (1972)], oxytocin, calcitonin, parathyroid hormone, glucagon, gastrin, vasoactive intestinal peptide (VIP), lipocortin, vasocortin, atrial natriuretic hormone (ANP), secretin, pancreozymin, cholecystokinin, angiotensin, human placental lactogen, human chorionic gonadotropin (HCG), enkephalin, enkephalin derivatives [European Patent Application Laid-Open No. 31567], endorphin, kyotorphin, interferon (alpha-, beta-, and gamma-), interleukin (I, II, III, IV, V, VI), tuftsin, thymopoietin, thymosin, thymostimulin, thymic humoral factor (THF), facteur thymique serique (FTS) and the derivatives thereof [Proc. Natl. Acad. Sci. U.S.A., Vol. 78, 1162–1166 (1981)], tumor necrosis factor (TNF), colony stimulating factor (CSF), motylin, dynorphin, bombesin, neurotensin, cerulein, bradykinin, urokinase, asparaginase, kallikrein, substance P, neurogrowth factor, blood coagulation factor VIII and IX, lysozyme chloride, polymyxin B, colistin, gramicidin, and bacitracin.

The said antibiotics include gentamicin, dibekacin, kanendomycin, lividomycin, tobramycin, amikacin, fradiomycin, tetracycline hydrochloride, oxytetracycline hydrochloride, rolitetracycline, doxycycline hydrochloride, ampicillin, piperacyllin, ticarcillin, cefalotin, cefaloridine, cefotiam, cefsulodin, cefmenoxime, cefmetazole, cefazolin, cefotaxime, cefoperazone, ceftizoxime, moxalactam, thienamycin, sulfazecin, and azthreonam.

The said antitumor agents include bleomycin hydrochloride, methotrexate, actinomycin D, mitomycin C, vinblastine sulfate, vincristine sulfate, daunorubicin hydrochloride, adriamycin, neocarzinostatin, cytosine arabinoside, 5-fluorouracil, tetrahydrofuryl-5-fluorouracil, krestin, picibanil, lentinan, levamisole, bestatin, azimexon, glicyrrhizin, polyI:C, polyA:U, and polyICLC.

The said antipyretics, analgesics, and antiphlogistics include sodium salicylate, sulpyrine, sodium fulfenamate, sodium diclofenac, sodium indometacin, morphine hydrochloride, pethidine hydrochloride, levorphanol tartarate, and oxymorphone; the said antitussive expectorants include ephedrine hydrochloride, methylephedrine hydrochloride, noscapine hydrochloride, codeine phosphate, dihydrocodeine phosphate, alloclamide hydrochloride, clofedanol hydrochloride, picoperidamine hydrochloride, cloperastine, protokylol hydrochloride, isoproterenol hydrochloride, salbutamol sulfate, and terubutaline sulfate; the said sedatives include chlorpromazine hydrochloride, prochlorperazine, trifluoperazine, atropine sulfate, and scopolamine methylbromide; the said muscle relaxants include pridinol methanesulfonate, tubocurarine chloride, and pancuronium bromide; the said antiepileptics include phenytoin sodium, ethosuximide, acetazolamide sodium, and chlordiazepoxide hydrochloride; the said antiulcer drugs include methoclopramide and histidine hydrochloride; the said antidepressants include imipramine, chlomipramine, noxyptiline, and phenelzine sulfate; the said antiallergic drugs include diphenhydramine hydrochloride, chlorpheniramine maleate, tripelennamine hydrochloride, methodilazine hydrochloride, clemizole hydrochloride, diphenylpyraline hydrochloride, and methoxyphenamine hydrochloride; the said cardiotonics include trans-$\pi$-oxocamphor, theophyllol, aminophylline, and etilefrine hydrochloride; the said antiarrhythmics include propranolol hydrochloride, alloprinol hydrochloride, bufetolol hydrochloride, and oxiprinol hydrochloride; the said vasodilators include oxyfedrine hydrochloride, diltiazem hydrochloride, tolazoline hydrochloride, hexobendine, and bamethan sulfate; the said hypotensive diuretics include hexamethonium bromide, pentolinium, mecamylamine hydrochloride, ecarazine hydrochloride, and clonidine hydrochloride; the said antidiabetics include glimidine sodium, glibizide, phenformin hydrochloride, buformin hydrochloride, and metoformin; the said anticoagulants include heparin sodium, and sodium citrate; the said hemostatics include thromboplastin, thrombin, menadione sodium bisulfite, acetomenaphthone, $\epsilon$-aminocaproic acid, tranexamic acid, carbazochrome sodium sulfonate, and adrenochrome monoaminoguanidine methanesulfonate; the said antitubercular agents include isoniazide, ethanebutol, and sodium p-aminosalicylate; the said hormones include predonisolone succinate, predonisolone sodium phosphate, dexamethasone sodium sulfate, betamethasone sodium sulfate, hexoestrol phosphate, hexoestrol acetate, and methimazole; the said narcotic antagonists include levallolphan tartarate, nalorphine hydrochloride, and naloxone hydrochloride.

The solutions of the water soluble drugs in this invention may be acidic, neutral, or basic, and therefore the drugs can be used advantageously for sustained release of acidic or neutral drugs, and for use of basic drugs at low concentrations.

This invention is particularly advantageous for production of sustained release preparations of neutral or basic polypeptides such as LH-RH, TRH, or the derivatives thereof.

The amount of the said water soluble drugs to be used varies according to the nature of the drug, the desired pharmacological effect, the duration of the effect, etc. In general, microcapsules of a water soluble drug are prepared by the in-water drying method or the phase separation method, wherein the concentration of the drug in the internal water phase or in the water phase is about 0.01% to about 90% (W/W), and preferably 0.1% to 80% (W/W).

The drug retaining substance in this invention need not shown high viscosity in the internal water phase or be solid or semisolid, and may be any organic substance as far as it has a positively charged basic residue, exerts no pharmacological effect at the dose used, and interacts with a polymer. In the embodiment wherein the drug is a water-soluble neutral or basic polypeptide, the drug retaining substance does not interact therewith.

Such organic basic substances are those of which the basic residue has a pKa of 8.0 or more, preferably 8.5 to 13.0, and the pH's of the aqueous solution (1.0 W/V %) thereof are 7.0 or more, preferably 7.6 to 13.0.

The said drug retaining substances are exemplified by basic amino acids, polypeptides containing basic amino acids, other organic bases such as basic derivatives of saccharides and natural or synthetic basic macromolecules.

The said basic amino acids include arginine ($pK_3 = 12.48$; pH10.8), lysine ($pK_3 = 10.53$; pH10.0), histidine ($pK_3 = 9.17$; pH7.8), and the derivatives thereof.

The said polypeptides including basic amino acids include L-Ala-L-His-L-Lys, L-Arg-L-Phe, Gly-L-His, Gly-L-His-Gly, Gly-L-His-L-Lys, L-His-Gly, L-His-Leu, L-His-L-Val, L-Lys-L-Tyr-L-Lys, L-His-L-Val, and L-Lys-L-Lys-L-Lys. The amino acids (residues) are expressed according to the IUPAC nomenclature.

The said organic bases include N-methylglucamine, and diethanolamine.

The said natural or synthetic basic macromolecules include chitosan, poly-L-lysine, and protamine.

Among these compounds, basic amino acids such as arginine, lysine, and histidine, basic derivatives of monosaccharides such as N-methylglucamine are particularly desirable.

These compounds may be used separately or in combination, and the amount to be used, though it varies according to the nature of the compound, is chosen from the range to make about 0.1% to 90% (W/W), preferably about 0.5% to 75% (W/W), in the (internal) water phase.

The said polymers are those which have acidic residues in the molecule, are practically insoluble or insoluble in water, and are compatible to organisms, and exemplified by biodegradable polymers, such as poly-fatty acid esters (polylactic acid, polyglycolic acid, polycitric acid, polymalic acid, polylactic caprolacton, etc.), poly-$\alpha$-cyanoacrylic esters, poly-$\beta$-hydroxybutyric acid, and polyamino acids (poly-$\gamma$-benzyl-L-glutamate, poly-$\gamma$-methyl-L-glutamate, etc.). Other macromolecules compatible to organisms include polyacrylic acid, polymethacrylic acid, copolymer of acrylic acid and methacrylic acid, and maleic anhydride copolymers. These polymers may be used separately or as copolymers or simple mixtures of two or more of them.

Among these polymers, biodegradable polymers are desirable particularly when used as injections; the most desirable polymers are polylactic acid, copolymers of lactic acid and glycolic acid, and the mixtures thereof.

Mean molecular weight of these polymers used in this invention is desirably about 1,000 to 800,000, preferably about 2,000 to 200,000.

When polylactic-glycolic acid is used as a high polymer, the molar ratio is desirably about 100/0 to 40/60.

The amount of a polymer to be used is dependent on the pharmacological activity of the water soluble drug used, rate and duration of release of the drug; for example, a polymer in the amount 1/5 to 10,000 times (by weight) that of the water soluble drug is used for the preparation, and preferably a polymer in the amount 1 to 1,000 times (by weight) that of the drug is used as the base for microcapsules.

The concentration of a polymer in the oil phase is about 0.5% to 90% (W/W), preferably about 2% to 60% (W/W).

The solution (the oil phase) containing the polymer described above is the solution wherein the polymer is dissolved in an oil phase.

The said solvents may be any solvents which have a boiling point below about 120° C., are immiscible with water, and dissolve a polymer, including halogenated alkanes (e.g. dichloromethane, chloroform, chloroethane, dichloroethane, trichloroethane, carbon tetrachloride, etc.), ethyl acetate, ethylether, cyclohexane, benzene, n-hexane, and toluene, which may be used as a mixture of two or more of them. The coacervating agents may be any of high molecular compounds such as mineral oils, and vegetable oils as far as they are miscible with the solvents for the polymers and do not dissolve the polymers for capsulation, including silicone oil, sesame oil, soybean oil, corn oil, cotton seed oil, coconut oil, linseed oil, and mineral oils, which may be used in combination of two or more of them.

The sustained release microcapsules of this invention are produced for example by the following method (in-water drying method). Namely, first a water soluble drug is dissolved in water to the concentration described above, to which a drug retaining substance is added to be dissolved or suspended to the concentration described above, which serves as the internal water phase.

To the internal phase, carbonic acid, acetic acid, oxalic acid, tartaric acid, succinic acid, malic acid, or a sodium or potasium salt thereof, hydrochloric acid, or sodium hydroxide may be added as an agent for pH adjustment to maintain the stability and solubility of the water soluble drug. In addition, as a stabilizer for the water soluble drug, albumin, gelatin, citric acid, sodium ethylenediamine tetraacetate, dextrin, or sodium bisulfite, or as a preservative, a p-hydroxybenzoate ester (methylparaben, propylparaben, etc.), benzylalcohol, chlorobutanol, or thimerosal may be added.

The internal water phase thus obtained is added to a solution containing a polymer (oil phase), which is then emulsified to give a W/O emulsion.

Emulsification is performed by the known methods of dispersion. The methods include the intermittent shaking method, the method using a mixer such as propeller mixer or turbine mixer, the colloid mill method, the homogenizer method, and the ultrasonic irradiation method.

Then the W/O emulsion thus prepared is used for preparation of microcapsules by the in-water drying method or the phase separation method. To prepare microcapsules by the in-water drying method, the W/O emulsion is added to a third water phase to constitute a W/O/W three-phased emulsion, followed by desorption of the solvent in the oil phase.

An emulsifier may be added to the outer water phase; the emulsifier may generally be any of those that constitute stable O/W emulsions, such as anion surfactants (sodium oleate, sodium stearate, sodium laurylsulfate, etc.), nonionic surfactants (poly(oxyethylene)sorbitan fatty acid esters [Tween 80, Tween 60, Atlas Powder Co.], polyoxyethylene castor oil derivatives [HCO-60, HCO-50, Nikko Chemicals Co.] etc.), polyvinylpyrrolidone, polyvinylalcohol, carboxymethylcellulose, lecithine, and gelatin, which may be used separately or in combination. The amount used may be chosen appropriately from the range of about 0.01% to 20%, preferably about 0.05% to 10%.

Desorption of the solvent in the oil phase is performed by the method usually employed; desorption is performed by gradual reduction of pressure by stirring with a propeller-type stirrer or a magnetic stirrer, or by adjusting the degree of vacuum with a rotary evaporator etc. The time required for this process can be shortened if mild warming of the W/O/W emulsion to facilitate desorption of the solvent is begun when the polymer has been solidified to some extent and the loss of the drug due to release from the internal water phase has been decreased.

Microcapsules thus obtained are collected by centrifugation or by filtration, followed by several repetitions of washing with distilled water to remove the free water soluble drug and the drug retaining substance adsorbed onto the surface of the capsules, and, if necessary, warming under reduced pressure, to complete desorption of the water in the microcapsules and desorption of the solvent in the membrane of the microcapsules.

When microcapsules are prepared by the phase separation method, the coacervating agent described above is added slowly to the said W/O emulsion by stirring, so that the polymer is deposited and solidified.

The microcapsules thus obtained are collected by filtration, followed by repeated washing with heptane etc. to remove the coacervating agent. Then removal of the free drug and desorption of the solvent are performed similarly as in the in-water drying method. For prevention of aggregation of particles during washing, an antiaggregation agent may be added.

The sustained release preparations of this invention are used for preparation of injections, oral drugs, transdermal drugs, transnasal drugs, rectal, urethral, and vaginal suppositories, etc.

Microcapsules prepared as described above are pulverized roughly and sieved so that too large microcapsules may be removed, if necessary. Particle size of microcapsules depends on the desired degree of sustained release, being in the range wherein the microcapsules can disperse enough and pass through the injection needle; for example, the mean particle radius is desirably about 0.5 to 400 $\mu$m, preferably about 2 to 200 $\mu$m.

Accordingly, this invention makes it possible to enhance the trapping rate of a water soluble drug into microcapsules, and to produce microcapsules with a firm wall membrane which rarely allows initial excessive release.

In addition, the microcapsules of this invention have many advantages, for example, that the microcapsules rarely aggregate together during the processes for preparation so that uniform spherical microcapsules with a given particle size are obtained, and that the removal of the solvent in the oil phase can be controlled easily so that the surface structure of the microcapsules which determines the rate of release of the drug (e.g. number and size of pores through which the drug is released) can be modified.

The microcapsules produced according to this invention can be administered without being processed any further in the form of injections or pellets into the muscle, subcutis, blood vessels, organs, joint cavity, lesions such as tumor, etc. They may also be administered after processing into various preparations, that is, they may be used as starting materials for production of such preparations.

For example, the microcapsules of this invention are processed into practically usable sustained release injections by preparing an aqueous suspension together with a disperser (e.g., Tween 80, HCO-60, carboxymethylcellulose, sodium alginate), a preservative (e.g., methylparaben, propylparaben), and a tonicity agent (e.g., sodium chloride, mannitol, sorbitol, glucose), or by preparing an oily suspension by dispersion together with a vegetable oil such as sesame oil or corn oil.

The sustained release injections containing the microcapsules can be processed into more stable, sustained release injections by redispersion by addition of an excipient as an additional suspending agent (e.g. mannitol, sorbitol, lactose, glucose) followed by freeze-drying or spray drying, and the injections are treated with distilled water for injection or an appropriate dispersion medium before use.

The dose of the sustained release preparations of this invention varies according to the nature and the content of the water soluble drug as the basis, the drug form, duration of release of the drug, the subject to be treated [e.g., warm-blooded mammals (e.g., mouse, rat, horse, cow, human)], and the purpose of treatment, being any effective dose of the water soluble drug. For example, a unit dose for one of the warm-blooded animals described above is desirably about 0.1 mg to 100 mg of the microcapsules/kg body weight, preferably about 0.2 mg to 50 mg/kg body weight.

As described above, pharmaceutical compositions prepared as microcapsules can be obtained which are composed of a water soluble drug of an effective dose exceeding a usual unit dose and a polymer compatible to organisms, and which can release the drug persistently over a long period with little initial burst.

In the present invention, it is assumed that a firm membrane of microcapsules is formed by interaction between the acidic residues of the polymer and the basic residues of the drug retaining substance, and that the trapping rate is increased and undesirable excessive initial release is suppressed by the decreased diffusion rate near the surface of the microcapsules. Therefore, the higher the basicity and the more the number of the residues of a drug retaining substance, the more effectively the drug retaining substance can prevent the excessive initial release. When the water soluble drug included has basic residues, or when basic residues have been incorporated by reaction into the water soluble drug as a prodrug, the water soluble drug itself may serve as a drug retaining substance so that microcapsules as excellent as those described above are obtained.

The sustained release preparations produced according to the present invention are characterized as follows:

(1) An excellent sustained release of a water soluble drug can be attained in various drug forms; particularly for injections that are required to be administered over a long period for desirable therapeutic effect, the desired pharmacological effect is always attained by once-a-week, once-a-month, or once-a-year administration instead of daily administration; thus more stable, sustained release over a longer period is attained as compared with the conventional sustained release preparations.

(2) The injections prepared by using a biodegradable polymer do not require surgical treatment such as implantation, can be given subcutaneously, intramuscularly, into organs and lesions as easily as the common suspension injections, and need not be taken out again from the organisms.

(3) As compared with the conventional method for production that consists in preparation of a W/O/W emulsion followed by in-water drying, the water soluble drug as the basis can be included more effectively into microcapsules and at the same time fine, uniform, spherical microcapsules are obtained.

(4) As compared with the conventional method for production that consists in preparation of a W/O/W emulsion followed by in-water drying or the method based on phase separation, microcapsules with decreased unnecessarily excessive initial release can be obtained and processed into safer preparations for which the rate of release is more stabilized.

EXAMPLES

The following Examples will explain this invention in more detail.

EXAMPLE 1

Two mg of TRH (free form) was dissolved in 0.05 ml of water, in which 30 or 50 mg of N-methylglucamine as the drug retaining substance was dissolved or suspended. The solution or suspension was added to a solution of 1 g of a lactic acid-glycolic acid copolymer (lactic acid/glycolic acid: 75/25, weight-average molecular weight 14,000, abbreviated as PLGA hereinafter) in 1.6 g of dichloromethane, and mixed in a small homogenizer (Polytron manufactured by Chinematica Co., Switzerland) for 30 to 60 seconds, to give a W/O emulsion. This emulsion was poured into 100 ml of 0.1% solution of polyvinyl alcohol (PVA) in water and mixed in a small homogenizer to give a W/O/W emulsion. Then dichloromethane was evaporated from the W/O/W emulsion by stirring so that the internal W/O emulsion was solidified and collected by centrifugation. The pellet was dispersed again in distilled water and centrifuged again, so that the free drug and the free drug retaining substance were removed by washing.

The collected microcapsules were freeze-dried for more complete removal of solvent and water, and thus microcapsules were obtained as powders.

Table 1 lists the drug-trapping rate (the percentage of the amount actually incorporated relative to the amount used), and the residual percentage in the microcapsules after one day in the vitro dissolution test at 37° C. in phosphate buffer pH 7.0 of the TRH-including microcapsules prepared as described above and the microcapsules containing no N-methylglucamine prepared for comparison.

TABLE 1

| Lot | Concentration of N-methylglucamine[a] | Trapping rate (%) | Residual percentage after 1 day[b] |
|---|---|---|---|
| A-200T | 0 | 88.7 | 32.7 |
| M-203T | 3 | 76.2 | 59.9 |
| M-205T | 5 | 80.5 | 89.8 |

[a] percentage of the weight of N-methylglucamine to that of PLGA (%)
[b] 1/30 M phosphate buffer pH 7.0, at 37° C.

When N-methylglucamine was not used, the drug-trapping rate was high enough because basic TRH had been chosen as the drug, though the residual percentage after one day was 32.7%, indicating that 67.3% of TRH had been released.

In contrast, when N-methylglucamine was added to the concentration of 3 or 5%, release after one day (initial release) decreased with increase of the concentration, and thus better microcapsules could be prepared.

EXAMPLE 2

Instead of the water soluble drug, phenol red which is used commonly as a marker was used.

Two mg of phenol red was dissolved in 0.05 ml of water, in which 30 or 50 mg of arginine as the drug retaining substance was dissolved or suspended. The solution or suspension was then treated similarly as described in Example 1, to give microcapsules including phenol red.

Table 2 and Table 3 list the trapping rate, the initial burst, and the residual percentage after 1, 2, and 4 weeks.

TABLE 2

| Lot | Concentration of arginine[a] | Trapping rate (%) | Residual percentage after 1 day[b] |
|---|---|---|---|
| A-200P | 0 | 73.6 | 35.7 |
| A-203P | 3 | 80.8 | 75.2 |
| A-205P | 5 | 87.4 | 91.0 |

[a]percentage of the weight of arginine to that of PLGA (%)

TABLE 3

| Lot | Residual percentage (%) | | |
|---|---|---|---|
| | Week 1 | Week 2 | Week 4 |
| A-200P | 30.0 | 31.8 | 9.4 |
| A-203P | 72.0 | 67.3 | 31.9 |
| A-205P | 75.3 | 61.7 | 36.4 |

Microcapsules containing arginine showed increase of the trapping rate, an increase which is dependent on the concentration of arginine added, and also a remarkable increase of the residual percentage after 1 day. The microcapsules of phenol red prepared by addition of arginine to the concentration of 3 or 5% showed a small initial release followed by approximately zero-order release over 4 weeks or more.

EXAMPLE 3

Two mg of TRH was dissolved in 0.05 ml of water, in which 10, 50, 90, or 150 mg of histidine as the drug retaining substance was dissolved or suspended. The suspension was then treated similarly as described in Example 1, to give microcapsules including TRH.

Table 4 lists the initial burst of the microcapsules thus obtained.

TABLE 4

| Lot | Concentration of histidine[a] | Residual percentage after 1 day |
|---|---|---|
| A-200T | 0 | 32.7 |
| A-201T | 1 | 55.2 |
| A-205T | 5 | 71.0 |
| A-209T | 9 | 73.7 |
| A-215T | 15 | 75.5 |

[a]percentage of the weight of histidine to that of PLGA (%)

The initial burst after 1 day decreased markedly by addition of histidine; addition of histidine to the concentration of 5 to 15% gave microcapsules with desirable release.

EXAMPLE 4

Two mg of methotrexate was dissolved in 0.1 ml of water, in which 20 or 30 mg of lysine as the drug retaining substance was dissolved. The solution was then treated similarly as described in Example 1, to give microcapsules including methotrexate.

Table 5 lists the initial burst of the microcapsules thus obtained.

TABLE 5

| Lot | Concentration of lysine[a] | Residual percentage after 1 day (%) |
|---|---|---|
| A-200M | 0 | 14.5 |
| A-202M | 2 | 81.2 |
| A-203M | 3 | 92.4 |

[a]percentage of the weight of lysine to that of PLGA (%)

The initial burst after 1 day decreased markedly by addition of lysine; addition of lysine to the concentration of 2 to 3% gave microcapsules with desirable release.

EXAMPLE 5

Two mg of 5-fluorouracil was dissolved in 0.1 ml of water, in which 20 or 30 mg of lysine as the drug retaining substance was dissolved. The solution was then treated similarly as described in Example 1, to give microcapsules including 5-fluorouracil.

Table 6 lists the initial burst of the microcapsules thus obtained.

TABLE 6

| Lot | Concentration of lysine[a] | Residual percentage after 1 day (%) |
|---|---|---|
| K-200F | 0 | 25.4 |
| K-202F | 2 | 66.9 |
| K-203F | 3 | 71.2 |

[a]percentage of the weight of lysine to that of PLGA (%)

The initial burst after 1 day was decreased markedly by addition of lysine; addition of lysine to the concentration of 2 or 3% gave microcapsules with desirable release.

EXAMPLE 6

Two mg of bleomycin hydrochloride was dissolved in 0.1 ml of water, in which 20 or 30 mg of lysine as the drug retaining substance was dissolved. The solution was then treated similarly as described in Example 1, to give microcapsules including bleomycin hydrochloride.

Table 7 lists the initial burst of the microcapsules thus obtained.

TABLE 7

| Lot | Concentration of lysine[a] | Residual percentage after 1 day (%) |
|---|---|---|
| K-200B | 0 | 29.8 |
| K-202B | 2 | 59.7 |
| K-203B | 3 | 74.8 |

[a]percentage of the weight of lysine to that of PLGA (%)

The initial burst after 1 day was decreased markedly by addition of lysine; addition of lysine to the concentration of 2 or 3% gave microcapsules with desirable release.

EXAMPLE 7

Ten mg of methotrexate was dissolved in 0.1 ml of water, in which 20 or 30 mg of L-Lys-L-Lys-L-Lys as drug retaining substance was dissolved by warming. The solution was then treated similarly as described in Example 1, to give microcapsules including methotrexate.

Table 8 lists the initial burst of the microcapsules thus obtained.

TABLE 8

| Lot | Concentration of L—Lys—L—Lys—L—Lys[a] | Residual percentage after 1 day (%) |
| --- | --- | --- |
| LL-200M | 0 | 21.8 |
| LL-202M | 2 | 72.9 |
| LL-203M | 3 | 85.4 |

[a] percentage of the weight of L—Lys—L—Lys—L—Lys to that of PLGA (%)

What is claimed is:

1. A sustained release microcapsule, comprising:
   a) a wall made of a biocompatible polymer having acidic residues, selected from the group consisting of a homopolymer of lactic acid and a copolymer of lactic acid and glycolic acid;
   b) a water-soluble neutral or basic polypeptide within the microcapsule, the concentration of the water-soluble neutral or basic polypeptide in the internal water phase being from 0.1% to 80% (W/W); and
   c) an organic basic substance for regulating the release of the polypeptide which:
      1) has a pKa at least 8.0;
      2) is selected from the group consisting of N-methylglucamine, diethanolamine, arginine, lysine and histidine;
      3) interacts with the acidic residues of the wall of the biocompatible polymer;
      4) does not interact with the water-soluble neutral or basic polypeptide;
      5) is added to the internal water phase at a concentration from 0.5% to 75% (W/W).

2. The microcapsule according to claim 1, wherein the basic substance is N-methylglucamine or diethanolamine.

3. The microcapsule according to claim 1, wherein the basic substance is arginine, lysine or histidine.

4. The microcapsule according to claim 1, wherein the water-soluble neutral or basic polypeptide is luteinizing hormone-releasing hormone, luteinizing hormone-releasing hormone derivative, thyrotropin-releasing hormone or thyrotropin-releasing hormone derivative.

5. A method of producing the microcapsule according to claim 1, which comprises:
   a) dissolving the water-soluble neutral or basic polypeptide in water; then
   b) dissolving or suspending the organic basic substance therein to form an internal water phase; then
   c) adding the internal water phase to an oil phase containing the biocompatible polymer having acidic residues, and emulsifying to make a w/o emulsion; then
   d) i) adding the w/o emulsion to a third water phase to make a w/o/w three-phased emulsion and then drying the w/o/w emulsion, or ii) adding a coacervation agent to the w/o emulsion under stirring to deposit and solidify the w/o emulsion, filtering and washing the resulting microcapsules, and then drying the microcapsules.

* * * * *